United States Patent
Yanson et al.

(10) Patent No.: US 10,773,249 B2
(45) Date of Patent: Sep. 15, 2020

(54) PREPARATION OF A ZSM-5-BASED CATALYST; USE IN ETHYLBENZENE DEALKYLATION PROCESS

(71) Applicant: SHELL OIL COMPANY, Houston, TX (US)

(72) Inventors: Yuriy Yanson, Amsterdam (NL); David Allen Cooper, Morrisville, PA (US); Hong-Xin Li, Lansdale, PA (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/312,418

(22) PCT Filed: Jun. 27, 2017

(86) PCT No.: PCT/EP2017/065789
§ 371 (c)(1),
(2) Date: Dec. 21, 2018

(87) PCT Pub. No.: WO2018/002012
PCT Pub. Date: Jan. 4, 2018

(65) Prior Publication Data
US 2019/0232261 A1  Aug. 1, 2019

(30) Foreign Application Priority Data

Jun. 29, 2016 (EP) .................................. 16176977

(51) Int. Cl.
| | |
|---|---|
| *B01J 29/44* | (2006.01) |
| *B01J 37/18* | (2006.01) |
| *B01J 29/48* | (2006.01) |
| *B01J 35/02* | (2006.01) |
| *B01J 35/10* | (2006.01) |
| *C07C 4/18* | (2006.01) |
| *B01J 37/00* | (2006.01) |
| *B01J 29/42* | (2006.01) |
| *B01J 29/40* | (2006.01) |
| *B01J 37/04* | (2006.01) |
| *B01J 37/06* | (2006.01) |
| *B01J 37/08* | (2006.01) |
| *B01J 37/30* | (2006.01) |

(52) U.S. Cl.
CPC ............ *B01J 29/44* (2013.01); *B01J 29/405* (2013.01); *B01J 29/42* (2013.01); *B01J 29/48* (2013.01); *B01J 35/023* (2013.01); *B01J 35/108* (2013.01); *B01J 35/1019* (2013.01); *B01J 35/1038* (2013.01); *B01J 35/1061* (2013.01); *B01J 37/0009* (2013.01); *B01J 37/009* (2013.01); *B01J 37/0018* (2013.01); *B01J 37/04* (2013.01); *B01J 37/06* (2013.01); *B01J 37/08* (2013.01); *B01J 37/18* (2013.01); *B01J 37/30* (2013.01); *C07C 4/18* (2013.01); B01D 2255/504 (2013.01); B01J 29/40 (2013.01); B01J 2229/16 (2013.01); B01J 2229/20 (2013.01); B01J 2229/32 (2013.01); B01J 2229/38 (2013.01); B01J 2229/42 (2013.01); C07C 2529/40 (2013.01); C07C 2529/44 (2013.01); C07C 2529/48 (2013.01); Y02P 20/52 (2015.11)

(58) Field of Classification Search
CPC ........ B01J 29/44; B01J 29/42; B01J 37/0009; B01J 37/30; B01J 37/08; B01J 37/06; B01J 37/04; B01J 37/009; B01J 37/0018; B01J 29/405; B01J 35/108; B01J 35/1061; B01J 35/1038; B01J 35/1019; B01J 35/023; B01J 29/48; B01J 37/18; B01J 29/40; B01J 2229/42; B01J 2229/38; B01J 2229/32; B01J 2229/20; B01J 2229/16; C07C 4/18; C07C 2529/40; C07C 2529/48; C07C 2529/44; B01D 2255/504; Y02P 20/52
See application file for complete search history.

(56) References Cited

U.S. PATENT DOCUMENTS

| | | | | |
|---|---|---|---|---|
| 5,080,878 | A * | 1/1992 | Bowes | B01J 29/40 208/111.05 |
| 5,468,368 | A * | 11/1995 | Baker, Jr. | C10G 47/16 208/111.35 |
| 5,990,031 | A * | 11/1999 | Ghosh | B01J 29/06 502/64 |
| 2011/0282123 | A1* | 11/2011 | Corma | B01J 37/30 585/533 |
| 2012/0178615 | A1* | 7/2012 | Corma | B01J 29/7042 502/64 |
| 2013/0197290 | A1* | 8/2013 | Domokos | B01J 29/40 585/486 |

* cited by examiner

Primary Examiner — Ali Z Fadhel
(74) Attorney, Agent, or Firm — Charles W. Stewart

(57) ABSTRACT

A process of preparing a catalyst composition which process comprises the steps of (a) treating ZSM-5 zeolite with an alkaline solution having a pH of at least (8) followed by ion exchange to obtain a treated zeolite, (b) extruding a mixture of the treated zeolite and binder and contacting the zeolite with a fluorocompound containing solution, (c) increasing the temperature of the extrudates obtained in step (b) to at least 200° C., and (d) combining the extrudates obtained in step (c) with one or more metals selected from the group consisting of Group (10) and (11) of the IUPAC Periodic Table of Elements and a process for the conversion of an aromatic hydrocarbons containing feedstock using a catalyst composition prepared by such process.

14 Claims, No Drawings

PREPARATION OF A ZSM-5-BASED CATALYST; USE IN ETHYLBENZENE DEALKYLATION PROCESS

CROSS REFERENCE TO RELATED APPLICATIONS

This is a national stage application of International Application No. PCT/EP2017/065789, filed 27 Jun. 2017, which claims benefit of priority to European Patent Application No. 16176977.3, filed 29 Jun. 2016.

FIELD OF THE INVENTION

The present invention relates to a process for preparing a catalyst composition and a process for the conversion of an aromatic hydrocarbons containing feedstock using catalyst prepared by such process.

BACKGROUND OF THE INVENTION

Ethylbenzene is one of the aromatic hydrocarbons that can be obtained from naphtha pyrolysis or reformate. Reformate is an aromatic product obtained by the catalysed conversion of straight-run hydrocarbons boiling in the 70 to 190° C. range, such as straight-run naphtha. The reformate feedstock itself is obtained by fractionation or distillation of crude petroleum oil, its composition varying depending on the source of the crude oil, but generally having a low aromatics content. On conversion to reformate, the aromatics content is considerably increased and the resulting hydrocarbon mixture becomes highly desirable as a source of valuable chemical intermediates and as a component for gasoline. The principle components are a group of aromatics often referred to as BTX: benzene, toluene and the xylenes, including ethylbenzene. Other components may be present such as their hydrogenated homologues, e.g. cyclohexane.

Of the BTX group the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity and xylene isomerisation or transalkylation processes have been developed to increase the proportion of para-xylene.

A further process that the gasoline producer can utilize is the hydrodealkylation of ethylbenzene to benzene.

Generally, the gasoline producer will isolate BTX from the reformate stream, and then subject the BTX stream to xylene isomerisation with the aim of maximising the para-xylene component. Xylene isomerisation is a catalytic process. Some catalysts used in this process have the ability not just to isomerise xylenes but to simultaneously dealkylate the ethylbenzene component. Normally the para-xylene is then separated out to leave benzene, toluene (unless toluene conversion processes have already been applied) and the remaining mixed xylenes, including ethylbenzene. This BTX stream can either be converted by transalkylation to increase the yield of xylenes by contacting with a heavier hydrocarbon stream or can be converted by dealkylation to selectively eliminate ethylbenzene and to increase the yield of benzene, while allowing the xylenes to reach equilibrium concentrations. The latter process is the subject of the present invention.

In ethylbenzene dealkylation at this latter stage of BTX treatment, it is a primary concern to ensure not just a high degree of conversion to benzene but also to avoid xylene loss. Xylenes may typically be lost due to transalkylation, e.g. between benzene and xylene to give toluene, or by addition of hydrogen to form, for example, alkenes or alkanes.

EP2027917 describes an ethylbenzene dealkylation catalyst which is prepared by mixing at least 20% wt of ZSM-5 having a bulk silica to alumina ratio in the range of from 20 to 150 and being in its H+ form with at least 30% wt of a binder selected from silica, zirconia and titania, drying and calcining the extrudates obtained, incorporating platinum and tin into the calcined extrudates, and drying and calcining the metal containing composition thus obtained. It does not mention the para-xylene content of product obtained in a dealkylation process using such catalyst.

US20130197290 describes an ethylbenzene dealkylation catalyst which is prepared by mixing and extruding ZSM-5 having a bulk silica to alumina ratio in the range of from 20 to 150 with water, a silica source and an alkali metal salt, drying and calcining the extrudates obtained, subjecting the calcined extrudates to ion exchange to reduce the alkali metal content, drying the ion exchanged extrudates, incorporating platinum and tin into the dried extrudates and drying and calcining the metal containing composition thus obtained. The para-xylene content of product obtained in a dealkylation process using such catalyst has not been described.

US20160017238 describes a catalyst for converting solid biomass into fuel of specialty chemical products.

U.S. Pat. No. 4,511,547 describes a process for preparing crystalline aluminosilicate zeolite.

The article by Christensen et al.: "Mesoporous zeolite single crystal catalysts: Diffusion and catalysis in hierarchical zeolites", Catalysis Today, Elsevier NL, vol. 128, no. 3-4, 30 Oct. 2007, pages 117-122, describes the use of mesoporous zeolite catalysts in alkylation of benzene with ethene. Analysis of the results obtained suggests that beneficial effect of mesopores also should be observed in the dealkylation of ethylbenzene. The para-xylene content of product obtained in a dealkylation process using such catalyst has not been described.

SUMMARY OF THE INVENTION

It is advantageous if a catalyst would be able to convert ethylbenzene to benzene while obtaining a product having increased para-xylene content. It would be especially advantageous if such alkylaromatic conversion process could be carried out at limited xylene loss. A process would be especially advantageous if it can be operated at relatively high weight hourly space velocity.

The present process of preparing a catalyst composition comprises the steps of
(a) treating ZSM-5 zeolite with an alkaline solution having a pH of at least 8 followed by ion exchange to obtain a treated zeolite,
(b) extruding a mixture of the treated zeolite and binder and contacting the zeolite with fluorocompound containing solution,
(c) increasing the temperature of the extrudates obtained in step (b) to at least 200° C., and
(d) combining the extrudates obtained in step (c) with one or more metals selected from the group consisting of Group 10 and 11 of the IUPAC Periodic Table of Elements.

A further process concerns conversion of an aromatic hydrocarbons containing feedstock using a catalyst composition prepared according to the above process.

DETAILED DESCRIPTION OF THE INVENTION

The ZSM-5 for use in the present invention preferably has a silica to alumina molar ratio (SAR) of at least 25, most preferably at least 30, and is preferably at most 100, most preferably at most 90, especially at most 50. Most preferably, the SAR is of from 35 to 50.

The bulk or overall SAR can be determined by any one of a number of chemical analysis techniques. Such techniques include X-ray fluorescence, atomic adsorption, and inductive coupled plasma-atomic emission spectroscopy (ICP-AES). All techniques will provide substantially the same bulk ratio value. The silica to alumina molar ratio for use in the present invention is determined by X-ray fluorescence.

The zeolite can exist in a number of particle size ranges. Generally, the ZSM-5 may have a number average particle size of from 20 nm to 30 µm. Useful catalysts have been prepared using a large crystal size ZSM-5 zeolite having a number average crystallite size in the range of from 1 to 30 micrometer, and also using a small particle size ZSM-5 having a number average particle diameter of from 20 to 200 nm. The large crystal size ZSM-5 is preferred.

The ZSM-5 preferably has a ratio of the average SAR at the edge of the crystallite to the average SAR at the center of the crystallite of greater than 1.15, more preferably at least 3. The SAR in these cases is measured by elemental maps produced from energy dispersive X-ray spectroscopy (EDX) coupled with transmission electron microscopy (TEM).

Most preferably, the ZSM-5 for use in the present invention is prepared by synthesis from an aqueous reaction mixture comprising an alumina source, a silica source, an alkali source and L-tartaric acid or a water-soluble salt thereof. Full details on ZSM-5 which preferably is used in the present invention are described in U.S. Pat. No. 8,574,542.

The ZSM-5 is treated in step (a) with an alkaline solution having a pH of at least 8. Suitable alkaline solutions have a pH of from 8 to 15, more preferably of from 9 to 15, more preferably of from 10 to 14, more specifically of from 11 to 14. Preferred solutions comprise metal hydroxide, more preferably alkali metal hydroxides and/or alkaline earth metal hydroxides. Most preferably, the alkaline solution is an aqueous solution comprising of from 5 to 30% wt of alkali metal hydroxide. The most preferred alkali metal hydroxides are potassium hydroxide and sodium hydroxide. Preferably, the zeolite is washed with water after having been treated with the alkaline solution and before being subjected to ion exchange. Without wishing to be bound to any theory, it is thought that the treatment with the alkaline solution removes silicon and/or silica from ZSM-5.

The ZSM-5 treated with an alkaline solution is subsequently subjected to ion exchange. The ion exchange can be carried out in any way known to the person skilled in the art such as treating the zeolite with an aqueous solution of a salt. The alkaline solution treated zeolite preferably is washed with water and dried before being subjected to ion exchange. Preferably, the zeolite is treated with an ammonium containing solution. Most preferably, the zeolite is treated with a solution containing an ammonium salt more preferably ammonium nitrate.

The ZSM-5 obtained in step (a) preferably has a mesopore volume of from 0.05 to 0.12 ml/g. The mesopores, as the term is used herein, are those pores of the ZSM-5 having a pore diameter in the range of from 50 to 350 angstroms (Å). The ZSM-5 obtained in step (a) preferably has a micropore volume of from 0.10 to 0.15 ml/g. The micropores, as the term is used herein, are those pores of the catalyst having a pore diameter less than 50 angstroms (Å). The ZSM-5 obtained in step (a) preferably has a mesopore BET surface area of from 70 to 200 $m^2/g$. The micropore and the mesopore volume each are derived from the nitrogen adsorption and desorption isotherm measured according to ASTM D4222-03. The mesopore BET surface area is measured according to ASTM D4365-13.

Zeolite obtained in step (a) is mixed with binder. Preferably, the binder is a refractory oxide, more preferably a refractory oxide selected from the group consisting of silica, zirconia, titania and mixtures thereof.

Most preferably, silica is used as a binder in the catalyst composition of the present invention. It may be naturally occurring silica or may be in the form of a gelatinous precipitate, sol or gel. The form of silica is not limited and the silica may be in any of its various forms: crystalline silica, vitreous silica or amorphous silica. The term amorphous silica encompasses the wet process types, including precipitated silicas and silica gels, or pyrogenic or fumed silicas. Silica sols or colloidal silicas are non-settling dispersions of amorphous silicas in a liquid, usually water, typically stabilized by anions, cations, or non-ionic materials.

The silica binder preferably is a mixture of two silica types, most preferably a mixture of a powder form silica and a silica sol. Conveniently powder form silica has a B.E.T. surface area in the range of from 50 to 1000 $m^2/g$; and a mean particle size in the range of from 2 nm to 200 micrometer, preferably in the range of from 2 to 100 micrometer, more preferably 2 to 60 micrometer, especially 2 to 10 micrometer as measured by ASTM C 690-1992 or ISO 8130-1. A very suitable powder form silica material is Sipernat 50, a white silica powder having predominantly spherical particles, available from Degussa (Sipernat is a trade name). A very suitable silica sol is that sold under the trade name of Bindzil by Eka Chemicals. Where the mixture comprises powder form silica and a silica sol, then the two components may be present in a weight ratio of powder form to sol form in the range of from 1:1 to 10:1, preferably 2:1 to 5:1, more preferably from 2:1 to 3:1. The binder may also consist essentially of just the powder form silica.

Where solely a powder form of silica is used as a binder in the catalyst composition of the present invention, preferably a small particulate form is utilized, which has a mean particle size in the range of from 2 to 10 micron as measured by ASTM C 690-1992. An additional improvement in carrier strength is found with such materials. A very suitable small particulate form is that available from Degussa under the trade name Sipernat 500LS.

Preferably the silica component is used as pure silica and not in combination with other refractory oxide components. It is most preferred that the silica is essentially free of any other inorganic oxide binder material, and especially is free of alumina. At most only a maximum of 2 wt % alumina, based on the total refractory oxide binder, is present.

The carrier of the present invention preferably comprises of from 10 to 70% wt of binder in combination with of from 30 to 90% wt of ZSM-5, more specifically of from 20 to 60% wt of binder in combination with of from 40 to 80% wt of ZSM-5, more specifically of from 25 to 55% wt of binder in combination with of from 45 to 75% wt of ZSM-5, most specifically 30 to 50% wt of binder in combination with of from 50 to 70% wt of ZSM-5.

The mixture of zeolite and refractory oxide binder may be shaped into any convenient form such as powders, extrudates, pills and granules. Preference is given to shaping by extrusion. To prepare extrudates, commonly the zeolite will be combined with the binder, preferably silica, and if necessary a peptizing agent, and mixed to form a dough or thick paste. The peptizing agent may be any material that will change the pH of the mixture sufficiently to induce deagglomeration of the solid particles. Peptizing agents are well known and encompass organic and inorganic acids, such as nitric acid, and alkaline materials such as ammonia, ammonium hydroxide, alkali metal hydroxides, preferably sodium hydroxide and potassium hydroxide, alkali earth hydroxides and organic amines, e.g. methylamine and ethylamine. Ammonia is a preferred peptizing agent and may be provided in any suitable form, for example via an ammonia precursor. Examples of ammonia precursors are ammonium hydroxide and urea. It is also possible for the ammonia to be present as part of the silica component, particularly where a silica sol is used, though additional ammonia may still be needed to impart the appropriate pH change. The amount of ammonia present during extrusion has been found to affect the pore structure of the extrudates which may provide advantageous properties. Suitably the amount of ammonia present during extrusion may be in the range of from 0 to 5 wt % based on the total dry mixture, preferably 0 to 3 wt %, more preferably 0 to 1.9 wt %, on dry basis.

In step (b) of the present process, the zeolite obtained in step (a) is contacted with a fluorocompound containing solution, preferably an aqueous solution. The fluorocompound can be fluorine as such or contain fluorine as part of a compound or salt. Without wishing to be bound by any theory, treating of the zeolite with fluorocompound containing solution is thought to dealuminate the zeolite. Fluorocompounds are capable of reacting with tetrahedral aluminum in the zeolite, generally by initial hydrolysis to fluoride ions which then extract aluminum from the framework as insoluble $AlF_3$, while a different element is then capable of entering the vacant sites resulting from the aluminum removal. Preferably, the solution contains ammonium fluoride.

The zeolite can be contacted with the fluorocompound as such or after having been incorporated into extrudates. Therefore, step (b) can comprise extruding a mixture of the treated zeolite and binder and subsequently treating the extrudates with a fluorocompound containing solution or step (b) can comprise contacting zeolite obtained in step (b) with a fluorocompound containing solution and subsequently mixing such zeolite with binder. In many cases, it is preferred to contact the zeolite containing extrudates with ammonium fluoride containing solution.

Most preferably, the zeolite is contacted with a solution of a compound chosen from the group consisting of fluorosilicates and fluorotitanates, most preferably a compound chosen from the group of fluorosilicates. These processes are described in more detail in U.S. Pat. No. 4,753,910. Most preferably, the fluorine treatment comprises contacting the zeolite with a solution of a fluorosilicate salt wherein the fluorosilicate salt is represented by the formula:

$$(A)_{2/b}SiF_6$$

wherein 'A' is a metallic or non-metallic cation other than H+ having the valence 'b'. Examples of cations 'b' are alkylammonium, $NH_4^+$, $Mg^{++}$, $Li^+$, $Na^+$, $K^+$, $Ba^{++}$, $Cd^{++}$, $Cu^+$, $Ca^{++}$, $Cs^+$, $Fe^{++}$, $Co^{++}$, $Pb^{++}$, $Mn^{++}$, $Rb^+$, $Ag^+$, $Sr^{++}$, $Tl^+$, and $Zn^{++}$. Preferably 'A' is the ammonium cation.

The solution comprising the fluorosilicate salt preferably is an aqueous solution. The concentration of the salt preferably is at least 0.005 mole of fluorosilicate salt/l, more preferably at least 0.007, most preferably at least 0.01 mole of fluorosilicate salt/l. The concentration preferably is at most 0.5 mole of fluorosilicate salt/l, more preferably at most 0.3, most preferably at most 0.1 of fluorosilicate salt/l. Preferably, the weight ratio of fluorosilicate salt solution to zeolite is from 50:1 to 1:4 of fluorosilicate solution to zeolite. If the zeolite is present together with binder, the binder is not taken into account for these weight ratios.

The pH of the aqueous fluorosilicate containing solution preferably is between 2 and 8, more preferably between 3 and 7.

The zeolite material preferably is contacted with the fluorosilicate salt solution for of from 0.5 to 20 hours, more specifically of from 1 to 10 hours. The temperature preferably is of from 10 to 120° C., more specifically of from 20 to 100° C. The amount of fluorosilicate salt preferably is at least 0.002 moles of fluorosilicate salt per 100 grams of total amount of zeolite, more specifically at least 0.003, more specifically at least 0.004, more specifically at least 0.005 moles of fluorosilicate salt per 100 grams of total amount of zeolite. The amount preferably is at most 0.5 moles of fluorosilicate salt per 100 grams of total amount of zeolite, more preferably at most 0.3, more preferably at most 0.1 moles of fluorosilicate salt per 100 grams of total amount of zeolite. If the zeolite is present together with binder, the binder is not taken into account for these weight ratios.

After shaping of the carrier, the carrier is subjected to a heat treatment which comprises increasing the temperature of the carrier to at least 200° C., more specifically of from 200 to 1000° C. The heat treatment comprises calcination which can be preceded by drying. Drying temperatures are suitably 50 to 200° C.; drying times are suitably from 0.5 to 5 hours. Calcination temperatures are very suitably in the range of from 200 to 800° C., preferably 300 to 600° C. For calcination of the carrier, a relatively short time period is required, for example 0.5 to 3 hours.

The catalyst of the present invention preferably comprises of from 0.001 to 5 wt % of one or more metals chosen from the group consisting of Groups 10 and 11, most preferably chosen from Group 10. Preferably, the metal is chosen from the group consisting of palladium and platinum. Most preferably, the catalyst comprises of from 0.001 to 0.1% wt of platinum and/or palladium, most preferably platinum, based on amount of metal on total amount of catalyst. The amount preferably is from 0.01 to 0.05% wt. Additionally, such catalyst can contain one or more further catalytically active metal compounds most preferably tin and/or rhenium, more specifically tin or rhenium.

The catalyst of the present invention may be prepared using standard techniques for combining the zeolite, binder such as silica, and optional other carrier components; shaping; compositing with the metals components; and any subsequent useful process steps such as drying, calcining, and reducing.

The metals emplacement onto the formed carrier may be by methods usual in the art. The metals can be deposited onto the carrier materials prior to shaping, but it is preferred to deposit them onto a shaped carrier.

Pore volume impregnation of the metals from a metal salt solution is a very suitable method of metals emplacement onto a shaped carrier. The metal salt solutions may have a pH in the range of from 1 to 12. The platinum salts that may conveniently be used are chloroplatinic acid and ammonium stabilized platinum salts.

After metals impregnation, the catalyst composition preferably is subjected to a heat treatment which comprises increasing the temperature of the carrier and catalyst composition, respectively, to at least 200° C., more specifically of from 200 to 1000° C. The heat treatment comprises calcination which can be preceded by drying. Drying temperatures are suitably 50 to 200° C.; drying times are suitably from 0.5 to 5 hours. Calcination temperatures are very suitably in the range of from 200 to 800° C., preferably 300 to 600° C. For calcination of the catalyst composition, it may be necessary to employ controlled temperature ramping at a low rate of heating to ensure the optimum dispersion of the metals. Such calcination may require from 5 to 20 hours.

Prior to use, it is generally preferred to ensure that the metals on the catalyst composition are in metallic (and not oxidic) form. Accordingly, it is useful to subject the composition to reducing conditions, which are, for example, heating in a reducing atmosphere, such as in hydrogen optionally diluted with an inert gas, or mixture of inert gases, such as nitrogen and carbon dioxide, at a temperature in the range of from 150 to 600° C. for from 0.5 to 5 hours.

The catalyst composition of the invention is especially suitable for use in conversion of aromatic hydrocarbons more specifically the selective dealkylation of ethylbenzene, more specifically dealkylation of ethylbenzene with simultaneous xylene isomerization.

The ethylbenzene feedstock most suitably originates directly from a reforming unit or naphtha pyrolysis unit or is the effluent of a xylene isomerisation unit. Such feedstock usually comprises hydrocarbons containing of from 7 to 9 carbon atoms, and in particular one or more of o-xylene, m-xylene, p-xylene, toluene, and benzene in addition to ethylbenzene. Generally, the amount of ethylbenzene in the feedstock is in the range of from 0.1 to 50 wt % and the total xylene content is typically at least 20 wt %, based on total amount of hydrocarbon feedstock. Typically, the xylenes will not be in a thermodynamic equilibrium, and the content of p-xylene will accordingly be lower than that of the other isomers compared with thermodynamic equilibrium.

The feedstock is contacted with the catalyst in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The process is suitably carried out at a temperature in the range of from 300 to 500° C., a pressure in the range of from 0.1 to 50 bar (10 to 5,000 kPa), using a weight hourly space velocity of in the range of from 0.5 to 20 g feed/g catalyst/hour. A partial pressure of hydrogen in the range of from 0.05 to 30 bar (5 to 3,000 kPa) is generally used. The feed to hydrogen molar ratio is in the range of from 0.5 to 100, generally from 1 to 10 mol/mol. As the catalyst of the present invention is especially suitable for use in high weight hourly space velocity processes, the preferred operating conditions comprise a weight hourly space velocity of in the range of from 7 to 17 g feed/g catalyst/hour, more specifically of from 8 to 14 g feed/g catalyst/hour, an overall pressure of from 5 to 25 bar (500 to 2,500 kPa), more specifically 8 to 15 bar (800 to 1,500 kPa) and a feed to hydrogen molar ratio in the range of from 1 to 5 mol/mol.

The present invention will now be illustrated by the following Examples.

EXAMPLES

Example 1

ZSM-5 was prepared as follows. 92 g of solid sodium hydroxide and 125 g of L-tartaric acid were dissolved in 3.5 l of water to which was then added 175 g of a sodium aluminate solution to prepare a homogeneous solution. Then, 660 g of silicic acid powder was added into this mixed solution slowly with stirring to prepare a homogeneously slurried aqueous reaction mixture. The reaction mixture was placed in an autoclave and, after closing the autoclave, it was allowed to react at 160° C. for 72 hours with stirring. Thereafter, the reaction product was taken out of the autoclave, washed with distilled water until its pH was almost neutral, then filtered and dried overnight at 120° C. The product thus obtained was the zeolite designated as "Original ZSM-5" and having the properties is shown in below Table 1. The product obtained had a crystal size of a few microns.

Alkali treated ZSM-5 was prepared as follows. 200 grams of 10% wt NaOH solution was added to a slurry comprising 188 g of ZSM-5 prepared as described above in 2000 g of water. The mixture obtained had a pH of 13.4 and was heated to 80° C. and held at that temperature during 2 hours. Subsequently, the solids were filtered off, washed with 3 liters of water and dried overnight at 100° C.

The dried product was added to a solution comprising 374 g ammonium nitrate and 2000 g of water. The mixture was heated to 70° C., held for 1 hour at 70° C., filtered and washed with water. The treatment with ammonium nitrate solution and water was repeated and finally the material was dried overnight at 100° C. The product thus obtained was the zeolite designated as "Alkali treated ZSM-5" and has the properties is shown in below Table 1.

TABLE 1

|  | Original ZSM-5 | Alkali treated ZSM-5 |
| --- | --- | --- |
| Molar silica to alumina ratio | 41 | 37 |
| Wt. % $Na_2O$ | 0.01 | 0.00 |
| BET surface area ($m^2/g$) | 438 | 451 |
| Micropore volume (cc/g) | 0.155 | 0.138 |
| Mesopore volume (cc/g) | 0.027 | 0.093 |
| Mesopore BET surface area ($m^2/g$) | 45 | 111 |
| Pore volume distribution (cc/g) |  |  |
| 260-600 A | 0.005 | 0.006 |
| 100-260 A | 0.003 | 0.006 |
| 50-100 A | 0.002 | 0.010 |
| 20-50 A | 0.018 | 0.070 |

The micropore and the mesopore volume each were derived from the nitrogen adsorption and desorption isotherm measured according to ASTM D4222-03. The mesopore BET surface area was measured according to ASTM D4365-13.

The zeolite powder was mixed with a low sodium grade silica (Sipernat 50 from Degussa), and an ammonium stabilized commercially available silica sol (sold under the trade name Bindzil by Eka Chemicals), and extruded using 1.5 wt % of ammonium hydroxide solution (containing 25 wt % ammonia) on dry basis to give a carrier comprised of 60 wt % zeolite, 26.7 wt % Sipernat 50 and 13.3 wt % silica sol on dry basis. The green extrudates were dried and calcined at about 550° C. for 1 hour to achieve sufficient strength for industrial application.

The resulting carrier contained 40% wt of silica binder and 60% wt of zeolite, based on dry weight.

Samples of each ZSM-5 and alkali treated ZSM-5 extrudates were calcined at 800° C. and subsequently treated with 0.02 M aqueous ammonium hexafluorosilicate solution. Thus treated samples were subsequently washed, dried and calcined.

Each of the above carriers was pore volume impregnated with a platinum containing solution having a pH below 2. The solution was prepared from H2PtCl6. The concentration of metal was such as to provide a final catalyst having a concentration of 0.025 wt %, based on total catalyst. Once the impregnation was completed, the catalyst was dried at 125° C. for 3 hours, and subsequently calcined in a two-step calcination program aiming at 480° C. with a sufficient low ramping rate to achieve adequate dispersion of the metallic phase. The total calcination procedure lasted 12 hours.

Example 2

Catalysts A, B, C and D as described in Table 3 were subjected to a catalytic test that mimics typical industrial application conditions for ethylbenzene dealkylation. This activity test used an industrial feed of which the composition is summarized in Table 2.

TABLE 2

| Composition of the feed used in the activity testing Feed composition | |
|---|---|
| EB wt % | 15.30 |
| pX wt % | 2.71 |
| oX wt % | 15.62 |
| mX wt % | 63.26 |
| toluene wt % | 0.28 |
| benzene wt % | 0.02 |
| C7-C8-naphthenes wt % | 2.81 |
| C9+ aromatics wt % | 0.00 |
| Total wt % | 100.00 |
| C8 aromatics sum wt % | 96.89 |
| EB in C 8 aromatics feed wt % | 15.79 |
| pX in xylenes in feed wt % | 3.32 |
| oX in xylenes in feed wt % | 19.14 |
| mX in xylenes in feed wt % | 77.53 |

The activity test was performed once the catalyst was in its reduced state, which was achieved by exposing the dried and calcined catalyst to atmospheric hydrogen (>99% purity) at 450° C. for 1 hour.

After reduction the reactor was pressurized without a cooling step, and the feed was introduced. This step contributed to enhanced catalyst aging, and therefore allowed comparison of the catalytic performance at stable operation.

The catalytic datapoints were collected at a condition that exaggerated the potential negative operational effects. Therefore, the performance was measured not at the ideal industrial operating conditions but at those that allow a better differentiation of the various performance parameters used to evaluate catalysts in this application.

In the present case, a weight hourly space velocity of 12 g feed/g catalyst/hour, a hydrogen to feed ratio of 2.5 mol·mol$^{-1}$ and a total system pressure of 1.2 MPa was used. The temperature was varied between 340 and 380° C. to achieve the required conversion for easier comparison.

The performance characteristics including the product obtained are shown in Table 2 below.

Ethylbenzene conversion (EB conversion) is the weight percent of ethylbenzene converted by the catalyst into benzene and ethylene, or other molecules. It is defined as wt % ethylbenzene in feed minutes wt % ethylbenzene in product divided by wt % ethylbenzene in feed times 100%.

PXate is a measure for the degree to which the xylene reaction mixture has reached equilibrium for para-xylene. It is defined as follows:

$$PXate = \frac{\% w\ PX\ \text{in Xylenes in product} - \% w\ PX\ \text{in Xylenes in feed}}{\% w\ PX\ \text{in Xylenes at equilibrium} - \% w\ PX\ \text{in Xylenes in feed}} \times 100\%$$

where PX stands for para-xylene.

Xylene loss is calculated as wt % xylenes in feed minus wt % xylenes in product divided by wt % xylenes in feed times 100%.

TABLE 3

| | Catalyst A (Comparative) Original ZSM-5, no fluorine treatment | Catalyst B (Comparative) Original ZSM-5, treated with fluorine | Catalyst C (Comparative) Alkali treated ZSM-5, no fluorine treatment | Catalyst D (According to the invention) Alkali treated ZSM-5, treated with fluorine |
|---|---|---|---|---|
| Reactor temperature (° C.) | 355 | 355 | 355 | 355 |
| EB conversion, wt % | 50.2 | 42.8 | 62.5 | 46.1 |
| pXate, % | 97.5 | 88.9 | 101.1 | 99.9 |
| Xylene loss, wt % | 2.68 | 1.02 | 5.00 | 1.24 |
| pX in product, wt % | 18.4 | 17.3 | 18.5 | 19 |

The above experimental results show that the present catalyst compositions provide an overall ethylbenzene to benzene conversion performance which increases the amount of para-xylene in the product. Moreover, the present catalysts allow converting ethylbenzene to benzene with limited xylene loss.

That which is claimed is:

1. A process of preparing a catalyst composition which process comprises the steps of:
   (a) treating ZSM-5 zeolite with an alkaline solution having a pH of at least 8 followed by ion exchange with an ammonium containing solution to obtain a treated zeolite,
   (b) extruding a mixture of the treated zeolite and a binder to form an extrudate and contacting the extrudate with a fluorocompound containing solution or contacting the treated zeolite with a flourocompound to form a contacted treated zeolite and extruding a mixture of the contacted treated zeolite with a binder to form an extradate,
   (c) increasing the temperature of the extrudates obtained in step (b) to at least 200° C., and
   (d) combining the extrudates obtained in step (c) with one or more metals selected from the group consisting of Group 10 and 11 of the IUPAC Periodic Table of Elements to form the catalyst composition.

2. The process according to claim 1 in which step (b) comprises extruding a mixture of the treated zeolite and silica binder, and subsequently treating the extrudates with a fluorocompound containing solution.

3. The process according to claim 2 in which step (b) comprises treating the extrudates with a solution comprising a fluorosilicate.

4. The process according to claim 1 in which the metal is selected from the group consisting of platinum and palladium.

5. The process according to claim 4 in which the extrudate is further combined with one or more metal chosen from the group consisting of tin and rhenium.

6. The process according to claim 1 in which the ZSM-5 zeolite to be treated in step (a) has silica to alumina molar ratio (SAR) of from 25 to 100.

7. The process according to claim 6 in which the ZSM-5 zeolite to be treated in step (a) has a SAR in the range of from 35 to 50.

8. The process according to claim 1 in which the ZSM-5 zeolite to be treated in step (a) has a number average particle size of from 20 nm to 30 micrometer.

9. The process according to claim 1 in which the catalyst composition comprises (i) ZSM-5 zeolite in an amount in the range of from 40 to 80 wt %, based on total weight of carrier, (ii) binder in an amount in the range of from 20 to 60 wt %, based on total weight of carrier; and (iii) of from 0.001 to 5 wt % of a metal selected from Group 10, based on total weight of catalyst.

10. The process according to claim 1 in which ZSM5 has been prepared from an aqueous mixture comprising an alumina source, a silica source, an alkali source and L-tartaric acid or a water-soluble salt thereof.

11. The process according to claim 1 in which the alkaline solution treatment of step (a) comprises treating ZSM-5 with a solution of a metal hydroxide.

12. The process according to claim 1 in which the ion exchange of step (a) comprises treating the zeolite with an ammonium containing solution.

13. A process for conversion of an aromatic hydrocarbons containing feedstock a comprising contacting the catalyst composition prepared according to claim 1 with the feedstock.

14. The process according to claim 13, wherein the feedstock comprises in the range of from 0.1 to 50 wt % of ethylbenzene and at least 20 wt % of xylene, all amounts based on total amount of hydrocarbon feedstock.

* * * * *